United States Patent
Van Neste et al.

(10) Patent No.: US 7,924,423 B2
(45) Date of Patent: Apr. 12, 2011

(54) REVERSE PHOTOACOUSTIC STANDOFF SPECTROSCOPY

(75) Inventors: Charles W. Van Neste, Kingston, TN (US); Lawrence R. Senesac, Knoxville, TN (US); Thomas G. Thundat, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 279 days.

(21) Appl. No.: 12/189,663

(22) Filed: Aug. 11, 2008

(65) Prior Publication Data

US 2010/0033720 A1 Feb. 11, 2010

(51) Int. Cl.
    *G01N 21/00* (2006.01)
(52) U.S. Cl. .......... 356/432; 356/300; 356/437
(58) Field of Classification Search .......... 356/432, 356/437, 300, 303, 326, 73
    See application file for complete search history.

(56) References Cited

U.S. PATENT DOCUMENTS

| | | | |
|---|---|---|---|
| 4,255,971 A | 3/1981 | Rosencwaig | |
| 4,276,780 A | 7/1981 | Patel et al. | |
| 4,543,486 A | 9/1985 | Rose | |
| 4,678,905 A | 7/1987 | Phillips | |
| 4,897,541 A | 1/1990 | Phillips | |
| 5,036,708 A | 8/1991 | Urban et al. | |
| 5,141,331 A | 8/1992 | Oehler et al. | |
| 5,285,677 A | 2/1994 | Oehler | |
| 5,319,977 A | 6/1994 | Quate et al. | |
| 5,360,268 A | 11/1994 | Hayashi et al. | |
| 5,391,001 A | 2/1995 | Rupert et al. | |
| 5,440,388 A | 8/1995 | Erickson | |
| 5,977,538 A | 11/1999 | Unger et al. | |
| 6,006,593 A | 12/1999 | Yamanaka | |
| 6,400,449 B2 | 6/2002 | Maris et al. | |
| 6,466,806 B1 | 10/2002 | Geva et al. | |
| 6,639,184 B1 | 10/2003 | Ennis | |
| 6,657,196 B2 | 12/2003 | Endo et al. | |
| 6,831,747 B2 | 12/2004 | Ferrell et al. | |
| 7,207,206 B2 | 4/2007 | Pinnaduwage et al. | |
| 7,243,548 B2 | 7/2007 | Thundat et al. | |
| 7,245,380 B2 * | 7/2007 | Kosterev ................ 356/437 |

(Continued)

FOREIGN PATENT DOCUMENTS

DE  39 25 312 A1  4/1990

(Continued)

OTHER PUBLICATIONS

PCT Seach Report and Written Opinion dated Dec. 14, 2009, PCT/US2009/052806, filed Aug. 5, 2009.

(Continued)

*Primary Examiner* — L. G Lauchman
(74) *Attorney, Agent, or Firm* — Brinks Hofer Gilson & Lione

(57) ABSTRACT

A system and method are disclosed for generating a reversed photoacoustic spectrum at a greater distance. A source may emit a beam to a target and a detector measures signals generated as a result of the beam being emitted on the target. By emitting a chopped/pulsed light beam to the target, it may be possible to determine the target's optical absorbance by monitoring the intensity of light collected at the detector at different wavelengths. As the wavelength of light is changed, the target may absorb or reject each optical frequency. Rejection may increase the intensity at the sensing element and absorption may decrease the intensity. Accordingly, an identifying spectrum of the target may be made with the intensity variation of the detector as a function of illuminating wavelength.

24 Claims, 5 Drawing Sheets

U.S. PATENT DOCUMENTS

| | | | |
|---|---|---|---|
| 7,326,580 | B2 | 2/2008 | Fukushima et al. |
| 7,411,189 | B2 | 8/2008 | Kawakatsu |
| 7,442,922 | B2 | 10/2008 | Knebel et al. |
| 7,448,269 | B2 | 11/2008 | Shekhawat et al. |
| 7,605,922 | B2 * | 10/2009 | Willing et al. ............ 356/437 |
| 7,665,364 | B2 * | 2/2010 | Su et al. .................... 73/643 |
| 7,691,583 | B2 | 4/2010 | Craighead |
| 2004/0085540 | A1 | 5/2004 | Lapotko et al. |
| 2004/0120577 | A1 | 6/2004 | Touzov |
| 2005/0070803 | A1 | 3/2005 | Cullum et al. |
| 2005/0117155 | A1 * | 6/2005 | Kosterev ............. 356/432 |
| 2005/0201661 | A1 | 9/2005 | Loock et al. |
| 2005/0244747 | A1 | 11/2005 | Nagai et al. |
| 2007/0175760 | A1 | 8/2007 | Thundat et al. |
| 2007/0220978 | A1 | 9/2007 | Su et al. |
| 2007/0220979 | A1 | 9/2007 | Su et al. |
| 2008/0094614 | A1 | 4/2008 | Tuschel et al. |
| 2008/0276695 | A1 | 11/2008 | Prater et al. |
| 2009/0174884 | A1 * | 7/2009 | Kosterev et al. ........ 356/432 |
| 2009/0321647 | A1 | 12/2009 | Shelley et al. |

FOREIGN PATENT DOCUMENTS

| | | |
|---|---|---|
| EP | 1 493 380 A1 | 1/2005 |
| JP | 11253794 A | 9/1999 |
| JP | 2001183294 A | 7/2001 |

OTHER PUBLICATIONS

Uotila, J, *A new design of the differential photoacoustic gas detector combined with a cantilever microphone*, The European Physical Journal, Special Topics, vol. 153, Mar. 12, 2008, pp. 401-404.

Koskinen, V. et al., *Cantilever enhanced photoacoustic detection of carbon dioxide using a tunable diode laser source*, Applied Physics B, Lasers and Optics, vol. 86, No. 3, Jan. 23, 2007, pp. 451-454.

Kosterev, A. et al., *Applications of quartz tuning forks in spectroscopic gas sensing*, Review of Scientific Instruments, vol. 76, No. 4, Mar. 23, 2005, pp. 043105-1 043105-9.

Su, X. et al., *Quartz tuning fork biosensor*, Biosensors and Bioelectronics, Elsevier, vol. 17, No. 1/02, Jan. 1, 2001, pp. 111-117.

Uotila, J and Kauppinen, Jyrki; *Fourier Transform Infrared Measurement of Solid-, Liquid-, and Gas-Phase Samples with a Single Photoacoustic Cell*; Applied Spectroscopy; vol. 62, No. 6; 2008; pp. 655-659.

Sievilia, P., Rytkonen, V-P, Hahtela, O, Chekurov, N., Kauppinen, J., Tittonen, I.; *Fabrication and characterization of an ultrasensitive acousto-optical cantilever*; Journal of Micromechanics and Microengineering; 17; 2007; pp. 852-859.

Lindley, R.E., Parkes, A.M., Keen, K.A., McNaghten, E.D., Orr-Ewing, A.J., *A sensitivity comparison of three photoacoustic cells containing a single microphone, a differential dual microphone or a cantilever pressure sensor*; Applied Physics B, Lasers and Optics; 86; 2007; pp. 707-713.

Koskinen, V., Fonsen, J., Kauppinen, J., Kauppinen, I., *Extremely sensitive trace gas analysis with modern photoacoustic spectroscopy*; Science Direct, Vibrational Spectroscopy; 42; 2006; pp. 239-242.

Ledermann, N., Muralt, P., Baborowski, J., Forster, M., Pellaux, J-P; *Piezoelectric Pb($Zr_x$, $Ti_{1-x}$)O3 thin film cantilever and bridge acoustic sensors for miniaturized photoacoustic gas detectors*; Journal of Micromechanics and Microengineering; 14; 2004; pp. 1650-1658.

Wells, P. N. T.; *A Vital Diagnostic Tool that Has Great Opportunities for Further Development*; IEEE Engineering in Medicine and Biology; Sep./Oct. 2000; pp. 14-20.

Crippa, P.R., Vecli, A., Viappiani, C.; *Time-resolved photoacoustic spectroscopy: new developments of an old idea*; New Trends in Photobiology (Invited Review); 24; 1994; pp. 3015.

PCT Seach Report and Written Opinion dated Feb. 6, 2010, PCT/US2009/052820, filed May 8, 2009.

C.W. Van Neste, L.R. Senesac, and T. Thundat, Standoff Detection of Explosive Residues Using Photothermal Microcantilevers, *Applied Physics Letters*, 92, 134102 (2008), © 2008 American Institute of Physics.

ORNL Demonstrates Super-Sensitive Explosives Detector, Oakridger.com, Jun. 30, 2008.

Waghe, A., Kanan, S.M., Abu-Yousef, I., Jensen, B., and Tripp, C., Infrared Study of UV-Irradiated Tungsten Trioxide Powders Containing Adsorbed Dimethyl Methyl Phosphonate and Trimethyl phosphate, *Res. Chem Intermed*, vol. 32, No. 7, pp. 613-623, 2006.

Yang, P.W. and Casal, H.L., In Situ Diffuse Reflectance Infrared Spectroscopic Study of the Photodecomposition of Dibenzyl Ketone Adsorbed on Zeolites, *J. Phys. Chem*, 90, pp. 2422-2424, 1986.

C.W. Van Neste, L.R. Senesac, and T. Thundat, Standoff Photoacoustic Spectroscopy, *Applied Physics Letters*, 92, 234102 (2008), © 2008 American Institute of Physics.

*XI International Scanning Probe Microscopy Conference 2009—Poster Session*; (8 pages).

Tetard et al., *New modes for subsurface atomic force microscopy through nanomechanical coupling*; Nature Nanotechnology (Letters) (Dec. 20, 2009); www.nature.com/naturenanotechnology.

*Crossing the line: how aggressive cells invade the brain*; R&D Mag Nov. 6, 2009; pp. 1-3; www.rdmag.com/.

Tetard et al., *Elastic phase response of silica nanoparticles buried in soft matter*; Applied Physics Letters 93; 133113 (Published on-line Oct. 2, 2008); pp. 133113-1-133113-3.

*First helium microscope is put through paces at NIST*; R&D Mag (Sep. 3, 2008); pp. 1-2; www.rdmag.com/News/2008/09/First-heliu—microscope-is-put-through-paces-at-NIST.

*WITec Microscope Technology Win Prestigious 2008 R&D 100*; Chemie.De (Jul. 10, 2008); vvww.chemie.ded/news/e/84528.

*WITec Microscope Technology Wins Prestigious 2008 R&D 100 Award*; WITec; Jul. 2008 www.witec.de/en/company/witecnews/news.php?id=37.

Tetard et al., *Imaging nanoparticles in cells by nanomechanical holography*; Nature Nanotechnology Letters (Jun. 22, 2008); pp. 501-505; www.nature.com/naturenanotechnology.

Wouters, et al., *Automated Scanning Probe Microscopy for Combinatorial Polymer Research*; Mater.Res.Soc.Symp.Proc.vol. 894 (2006), pp. 111-117.

Shekhawat et al., *Nanoscale Imaging of Buried Structures via Scanning Near-Field Ultrasound Holography*; Science Mag; vol. 310; Oct. 7, 2005; www.sciencemag.org; pp. 89-92.

Cuberes et al., *Heterodyne force microscopy of PMMA/rubber nanocomposites: nanomapping of viscoelastic response at ultrasonic frequencies*; J. Phys.D: Appl. Phys. 33 (2000); pp. 2347-2355.

Kolosov et al., Nonlinear Detection of Ultrasonic Vibrations in an Atomic Force Microscope; Jpn. J. Appl. Phys. vol. 32 (1993); pp. L 1095-L 1098.

Tetard et al., *New modes for subsurface atomic force microscopy through nanomechanical coupling*; Nature Nanotechnology (Supplementary Information); www.nature.com/naturenanotechnology; pp. 1-9, 20-28.

*AFM-Raman System*; Renishaw; pp. 1-3; http://www.renishaw.com/en/6638.aspx.

*MultiView 1000*; Nanonics Imaging Ltd.; pp. 1-7; http://www.nanonics.co.il/multiview-1000.html.

*MonoVista CRS*; Princeton Instruments; pp. 1-2; www.princetoninstruments.com/products/specsys/monovistacrs/.

*Alpha500 Automated Confocal Raman & Atomic Force Microscope*; WITec; www.witec.de.

*Alpha300A Atomic Force Microscope*; WITec; www.witec.de.

*Welcome to WITec*; WITec; www.witec-instruments.com/en/home/.

*Atomic Force Microscope alpha300 A*; WITec; www.witec-instruments.com/en/products/afm/alpha300a/.

*Confocal Raman and Atomic Force Microscope alpha 500*; WITec; www.witec-instruments.com/en/products/raman/alpha500/.

*Atomic force microscope*; Wikipedia, the free encyclopedia; pp. 1-7; http://en.wikipedia.org/wiki/Atomic_force_microscope.

*Lock-in Amplifier*; Wikipedia, the free encyclopedia; pp. 1-4 http://en.wikipedia.org/wiki/Lock-in_amplifier.

Google Search results for "mode synthesizing sensing atomic force microscopy", www.google.com/search?hl=en&ie=ISO-8859-1&q=mode+synthesizing+sensing+atomic+force+micro...; (2 pages).

\* cited by examiner

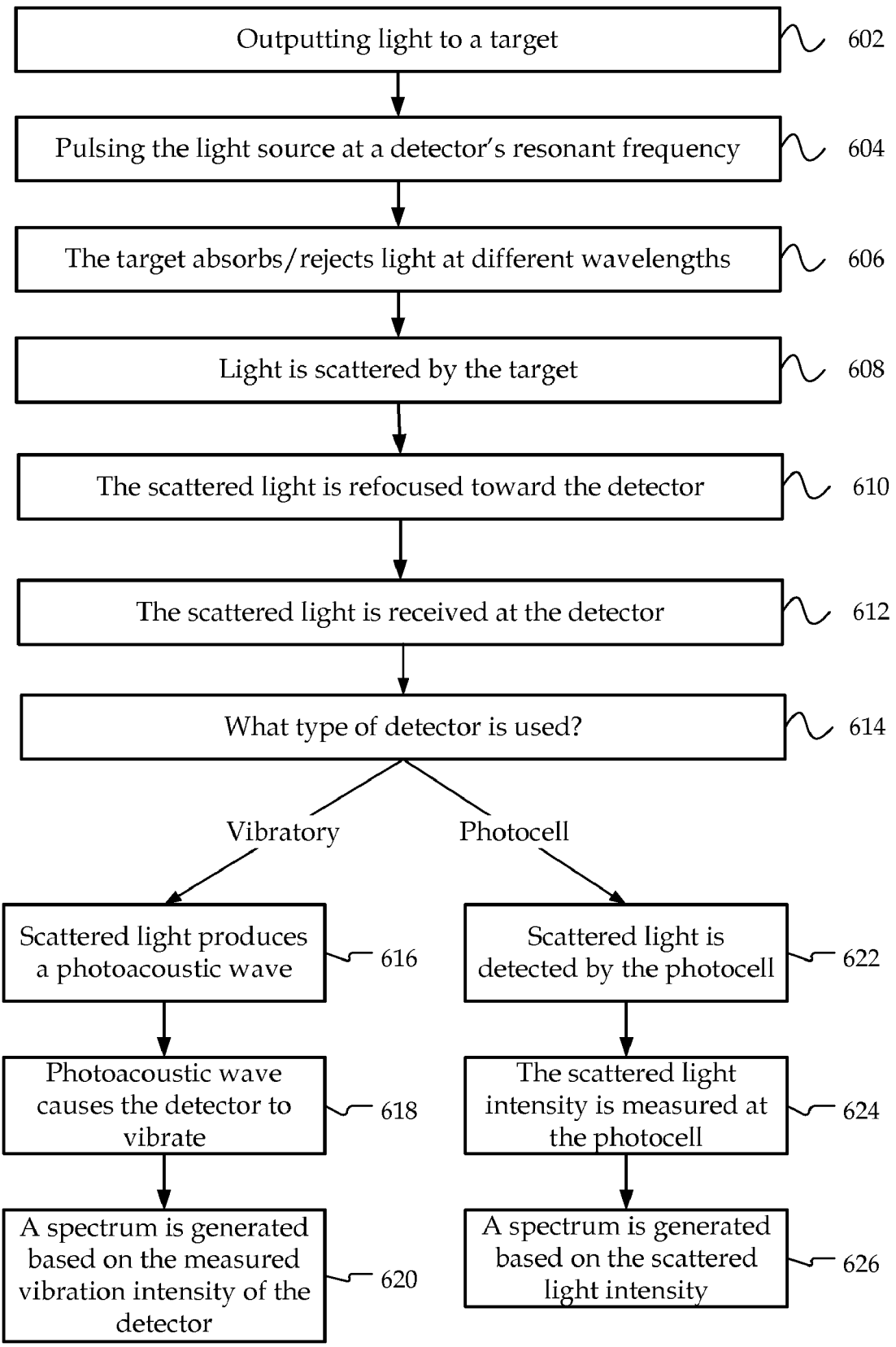

REVERSE PHOTOACOUSTIC STANDOFF SPECTROSCOPY

STATEMENT REGARDING FEDERALLY SPONSORED RESEARCH

This invention was made with government support under Contract No. DE-AC05-00OR22725 awarded by the U.S. Department of Energy. The government has certain rights in the invention.

RELATED APPLICATION

This application is related to the application entitled "PHOTOACOUSTIC POINT SPECTROSCOPY," filed on Aug. 11, 2008, U.S. Ser. No. 12/189,652, which is incorporated by reference.

BACKGROUND

Photoacoustic spectroscopy (PAS) may utilize the photoacoustic effect. The photoacoustic effect may include a conversion of light to acoustic waves due to absorption and localized thermal excitation. Light may be absorbed and transformed into kinetic energy. The absorption may result in local heating and a pressure/sound wave. A measurement of the sound waves at different wavelengths may be used to generate a photoacoustic spectrum of a sample. In an open environment, it may be difficult to detect these waves. The waves may spread and stretch their energy outward and they may be exposed to environmental noise, which may reduce the range and sensitivity for producing a photoacoustic spectrum.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

FIG. 6 is spectroscopy system with source and detector arrays.

DETAILED DESCRIPTION

By way of introduction, a system and method for generating a reversed photoacoustic spectrum at a greater distance are described. A source may emit a beam to a target and a detector measures signals generated as a result of the beam partially or fully returning to a detector positioned near said source. Absorption of pulsed light by the sample may result in the generation of sound. Absorption of light may also result in decreased reflection or scattering of the light by the sample. By emitting a chopped/pulsed light beam to the target, it may be possible to determine the target's optical absorbance by monitoring the intensity of light collected at a vibratory detector at different wavelengths. As the wavelength of light is changed, the target may absorb or reject each optical frequency. Rejection may increase the intensity at the sensing element and absorption may decrease the intensity. Accordingly, an identifying spectrum of the target may be made with the intensity variation of the detector signal as a function of illuminating wavelength. The detector may comprise a vibrating or oscillatory sensor and the observed spectrum may correspond with a reversed photoacoustic spectrum of the sample.

Figure 1:
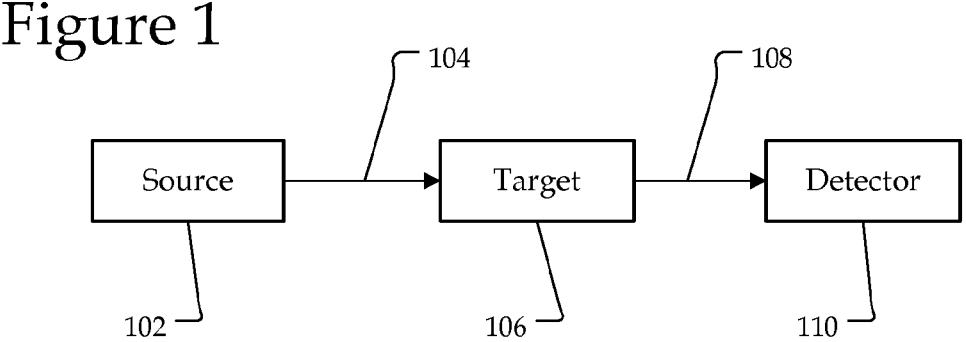
FIG. 1 illustrates an exemplary spectroscopy system.

Photoacoustic spectroscopy may measure the photoacoustic effect on a target substance or material. FIG. 1 illustrates an exemplary photoacoustic spectroscopy system. The spectroscopy system may include a source 102, a target 106, and a detector 110. The source 102 may include a beamformer or a light source, such as a laser, monochromator, light emitting diode (LED), diode laser, LED pile, or the sun with a grating. The source 102 may be tunable.

The source 102 may provide an optical beam 104 to a target 106. The optical beam 104 may include a light beam of any type or a laser emission. The light source may be oscillatory, such that the optical beam 104 is chopped or pulsed at a predetermined or adjustable frequency. The target 106 may be a solid, liquid, or gas. For example, the target 106 may be a residue, such as an explosives or gun powder residue that is to be identified. The target 106 may include a surface at an airport that is tested for explosive and/or other material residues. Alternatively, the target 106 may be human tissue or cells, such that a medical doctor may test for skin cancer or other skin conditions by analyzing a spectrum of light reflected off the skin. The spectra for cancer cells may be different from the spectra for normal cells. In another example, colon cancer may be detected when light is pumped through fiber optics along a colonoscopy tube. The doctor may view the abnormal areas and receive a confirmation using the spectra. This may be beneficial for testing lesions that are flat (early stages of colon cancer).

The analysis may identify or determine various properties of the target 106. The optical beam 104 may be partially absorbed and/or partially rejected by the target 106, such that the optical beam 104 may be scattered by the target 106 producing scattered light 108 that is monitored by a detector 110. The scattered light 108 may be the result of the optical beam 104 being reflected, diffracted, and/or rejected by the target 106.

The detector 110 may be a mechanical resonator that measures an acoustic signal. The scattered light 108 may produce acoustic waves on the surface of the detector 110 as a result of the photoacoustic effect. Changing the wavelength of the optical beam 104 may result in a change in wavelength of the scattered light 108. As the target absorbs or rejects the changing wavelength of the optical beam 104, the intensity of the scattered light 108 may also change. The intensity change of the scattered light 108 may change the intensity of the acoustic waves generated on the detector 110. The acoustic waves on the detector 110 may be analyzed to identify the target 108. The detector 110 may comprise a vibratory detector to measure the pulsed scattered light 108. The intensity of the generated scattered light 108 may be proportional to the intensity of the optical beam 104. The analysis may occur at the detector 110, or the detector 110 may be coupled with an analysis apparatus, such as a computer system for analyzing the signals of the detector 110.

Figure 2:
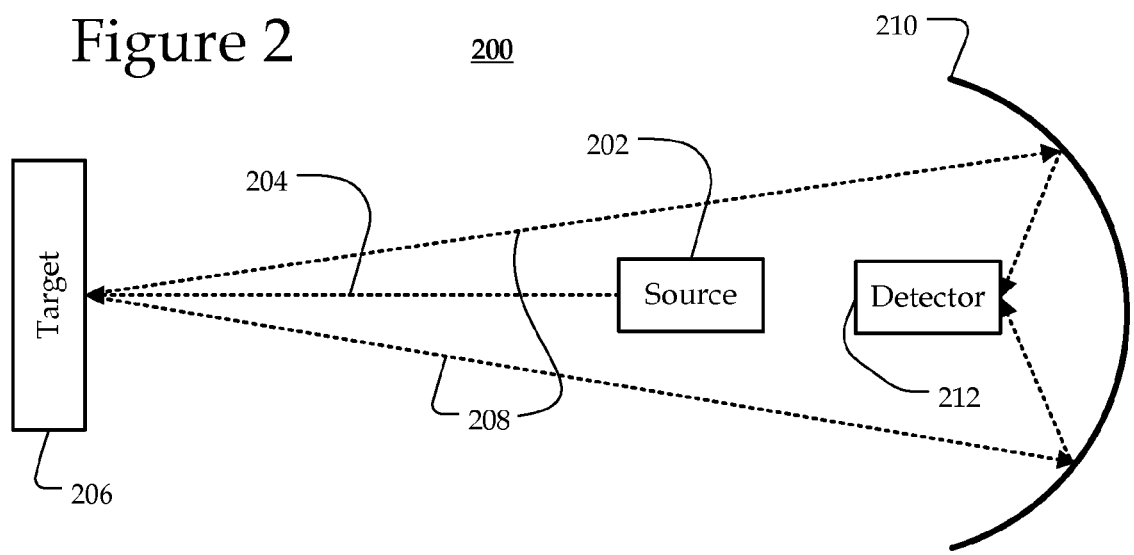
FIG. 2 illustrates an exemplary standoff spectroscopy system.

FIG. 2 illustrates an exemplary standoff spectroscopy system 200. The spectroscopy system 200 may include a source 202, a target 206, collection optics 210, and a detector 212. The source 202, target 206, and detector 212 may include the source, target and detector described with respect to FIG. 1.

The system 200 may include a quantum cascade laser source 202, a target 206, collection optics 210, and a quartz crystal tuning fork detector 212. The source 202 may emit an optical beam 204 on the target 206. The optical beam 204 is pulsed at the source 202 at the resonant frequency of the quartz crystal tuning fork. Certain optical wavelengths of the optical beam 204 will be absorbed by the target 206, while other frequencies may be rejected by the target 206. The rejection produces scattered light 208 from the target. The target 206 may absorb and reject some of the optical beam 204. The rejected portion of the optical beam 204 may result in scattered light 208, which is collected by the collection optics 210. The collection optics 210 may refocus the scattered light 208 onto the tine of the quartz crystal tuning fork detector 212. The collection optics 210 may be placed adjacent the source 202 and may be positioned at or near the collection optic's focal point.

The quantum cascade laser source 202 or quartz crystal tuning fork detector 212 may be modulated or regulated by adjusting its amplitude, by turning it on and off, or by combining its output with other instrumentation. The modulation may be a form of diphase modulation that is combined with signal conditioning. The modulation may be specific to the device or quartz crystal tuning fork detector 212. The optical beam 204 may be pulsed or chopped at or near a resonant frequency of the quartz crystal tuning fork detector 212 so that the scattered light 208 will produce a photoacoustic wave on the surface of the quartz crystal tuning fork detector 212 which may create a measurable vibration of the quartz crystal tuning fork detector 212. The photoacoustic wave may be measured and analyzed for determining various properties of the target 206. When the optical wavelength of the optical beam 204 is modified, the target 206 absorbs or rejects energy as the wavelengths are changed, and the intensity of the collected scattered light 208 at the quartz crystal tuning fork detector 212 increases or decreases. This may produce an increasing or decreasing photoacoustic wave on the surface of the quartz crystal tuning fork detector 212 which causes a mechanical vibration of quartz crystal tuning fork detector 212 to increase or decrease. The amplitude of vibration of the quartz crystal tuning fork detector 212 yields a reversed photoacoustic spectrum of the target 206 as a function of the detector's output signal verses optical wavelength.

Alternatively, the detector 212 may be a mechanical resonator that measures an acoustic signal produced on its surface. The scattered light 208 may produce acoustic waves on the detector's surface as a result of the photoacoustic effect, which the detector 212 measures generating a reversed photoacoustic spectrum. The optical beam 204 may have its intensity varied due to the absorption of the target 206, such that the scattered light 208 emitted at the different optical wavelengths may be analyzed for identifying the target 206. The detector 212 may be a vibratory detector to measure the pulsed scattered light 208 due to the pulsed optical beam 204 using the photoacoustic effect generated on the surface of the detector. The intensity of the generated photoacoustic waves on the surface of the detector may be proportional to the intensity of the scattered light 208 at each changing optical wavelength. The photoacoustic waves produced on the surface of the detector 212 may induce a mechanical vibration of the detector 212. The detector 212 may be coupled with an analysis apparatus, such as a computer system, for analyzing the target 206 through vibration of the detector 212.

Figure 3:
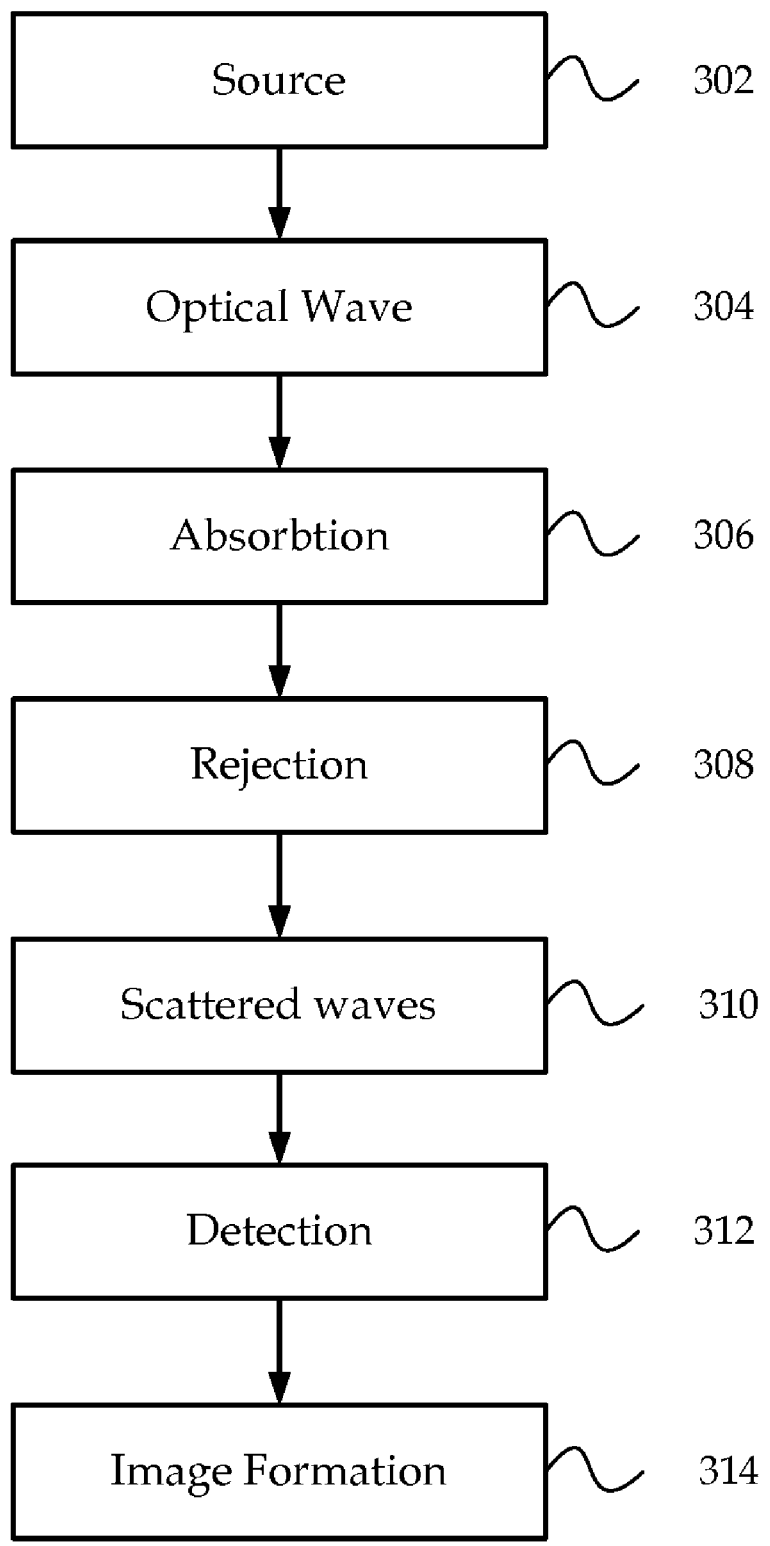
FIG. 3 illustrates exemplary photoacoustic imaging.

FIG. 3 illustrates exemplary photoacoustic imaging. A source 302 provides an optical wave 304 to a target. The optical wave 304 is pulsed or chopped before being partially or fully absorbed 306 by the target. Certain frequencies of the optical wave 304 will be absorbed, while other frequencies may be rejected 308 by the target. The rejection 308 produces scattered optical waves 310 from the target. The detection 312 of the scattered optical waves 310 may be used for forming an image 314. The detection 312 may include an amplification of the measured optical waves 310. For example, the detection 312 may include the collection and focusing of the scattered optical waves 310 on a microphone diaphragm or a quartz tuning fork tine that generates an acoustic wave on the surface of the microphone diaphragm or a quartz tuning fork tine used to create an image 314. The image formation 314 may be a reversed photoacoustic spectrum of the target that is used to identify that target. As the color of the optical wave 304 is changed, the target will absorb certain wavelengths (i.e. colors) better than others. This may vary the intensity of the scattered optical waves 310, which in turn may vary the acoustic waves generated at the detection 312.

Figure 4:
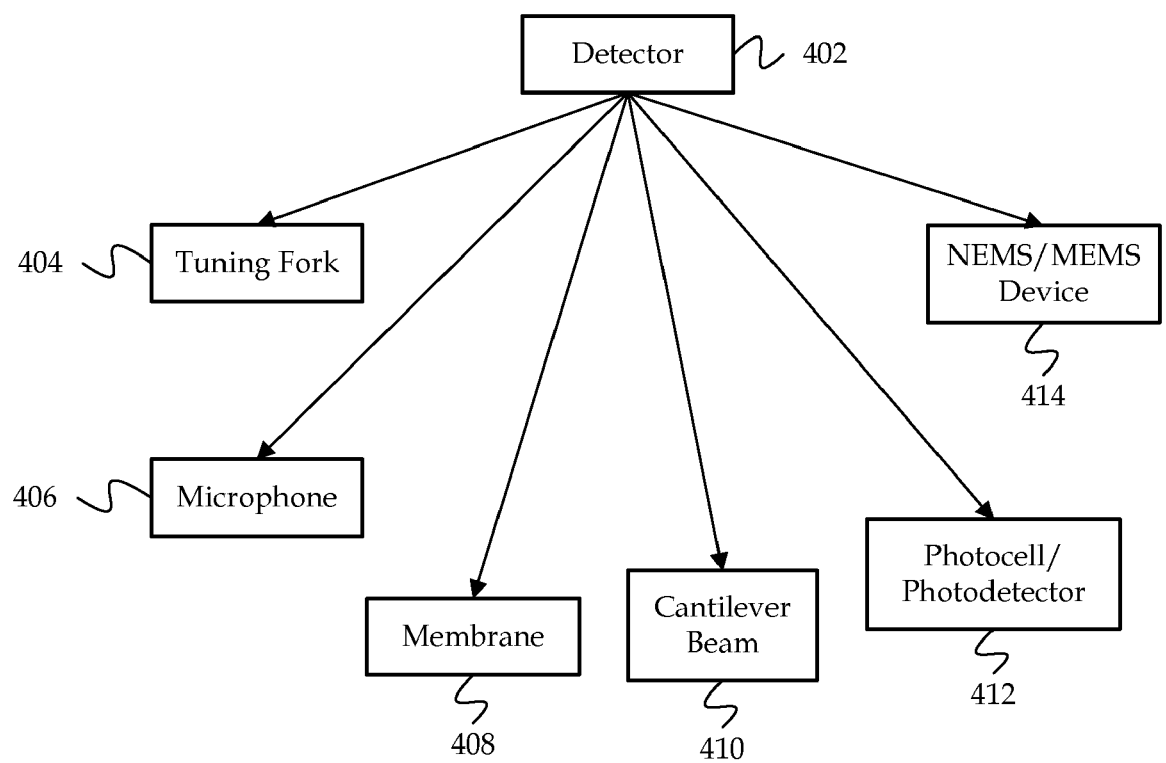
FIG. 4 is an embodiment of a remote spectroscopy system.

FIG. 4 illustrates exemplary detectors. The detector 110 and the detector 212 may comprise the detector 402 and/or the detection 212 may be performed by the detector 402. The detector 402 may comprise a tuning fork 404, microphone 406, membrane 408, cantilever beam 410, a photocell/photodetector 412, a Microelectromechanical System (MEMS) device, and/or a Nanoelectromechanical System (NEMS) device 414.

The tuning fork 404 may comprise a tuning fork made of any material, such as quartz. An exemplary quartz crystal tuning fork, such as those manufactured for wrist watches, may be used. An exemplary quartz crystal tuning fork may be quoted by the manufacturer as having a quality factor near 90,000 in a vacuum. In air, quartz crystal tuning forks may produce a sensitivity on the order of about 0.1 Hz. When pulsed light is allowed to hit one of the tines of the tuning fork, a photoacoustic pressure may develop at the air-surface interface. When the frequency of pulsed light is close to the resonant frequency of the tuning fork, an increased piezoelectric signal may be generated due to the piezoelectric material nature of quartz. A quartz crystal tuning fork resonator may benefit from sharp resonant peaks, lower purchasing cost, and a pulsed or chopped optical stimulation range from any optical frequency, including but not limited to ultraviolet (UV) through far infrared (IR).

The microphone 406 may be any microphone utilized to measure acoustic waves generated on the surface of the microphone's diaphragm as a result of the pulsed or chopped scattered light. Alternatively, the microphone 406 may be any acoustic transducer configured to measure acoustic waves. Likewise, the membrane 408, such as a NEMS or MEMS membrane, and the cantilever beam 410, such as a micro- or nano-cantilever beam may measure the acoustic waves.

The detector 402 may comprise a photocell 412 or a photodetector. The photocell 412 may measure the intensity of light directly. The photocell 412 may count photons to determine the amount of energy at each wavelength of light that it measures. Accordingly, as the target absorbs or rejects various optical wavelengths, the intensity of the light scattering off the target may change. The photocell 412 detects the intensity changes and produces a voltage accordingly. A spectrum of the target is produced as a function of the outputted photocell voltage and the optical wavelength of the optical beam from the source. The photocell 412 may include AC circuits for measuring oscillation, such as a pulsed source. Alternatively, the detector 402 may comprise any optical detector that measures changes in the light scattered by the target.

Alternatively, the detector 402 may comprise a NEMS/MEMS device 414 that may be any acoustic transducer fabricated to micrometer dimensions which may use other methods of sensing besides membranes and cantilevers. Likewise, the NEMS/MEMS device 414 may be any acoustic transducer fabricated to nanometer dimensions which may use other methods of sensing besides membranes and cantilevers.

Figure 5:
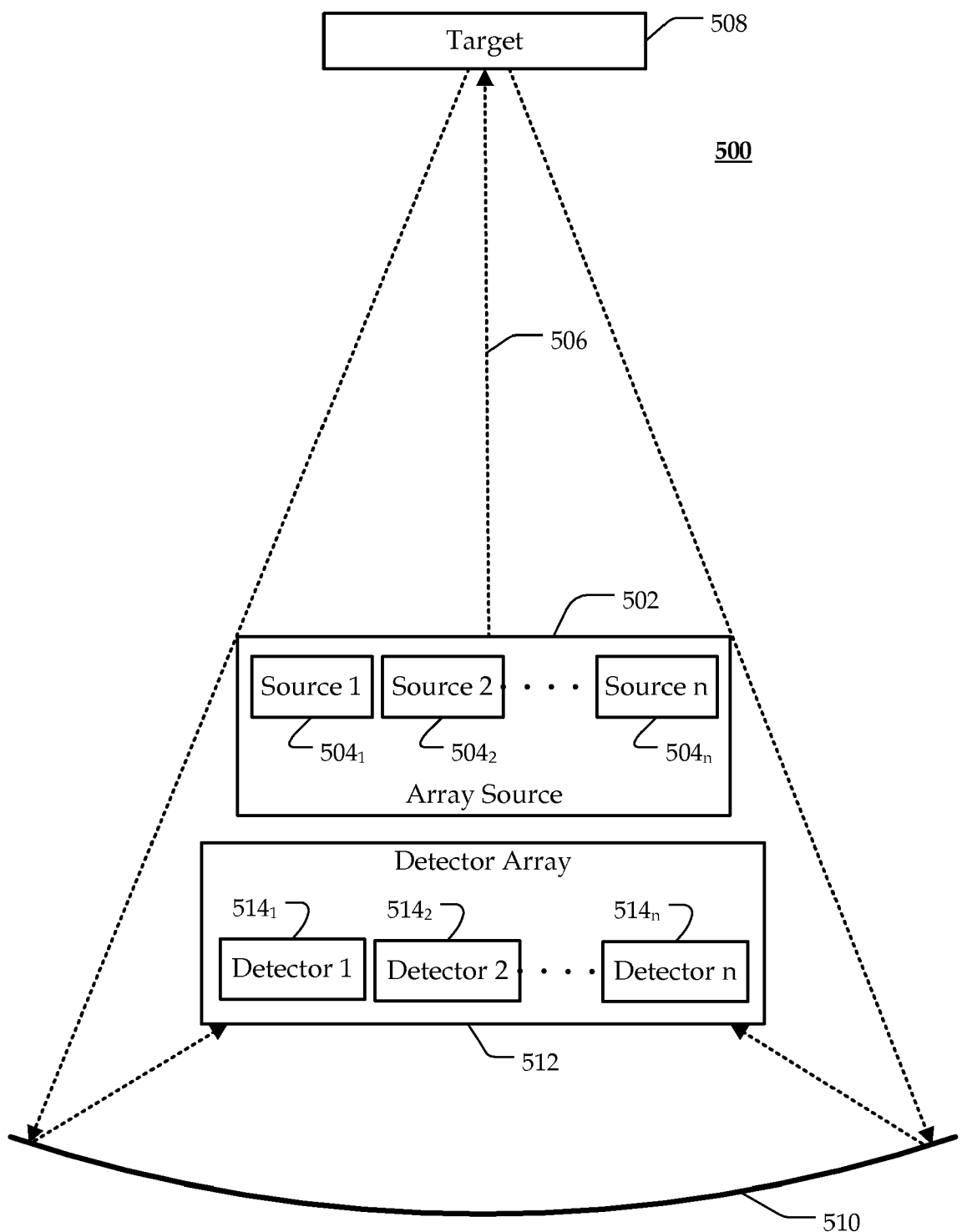
FIG. 5 illustrates exemplary detectors.

FIG. 5 is a standoff spectroscopy system 500 with source and detector arrays. The system 500 may include an array source 502, a target 508, collection optics 510, and a detector array 512. The array source 502 may include a plurality of sources 504, such as a first source $504_1$, a second source $504_2$, and additional sources up to an $n^{th}$ source $504_n$. The value of n may be any integer greater than or equal to one. The array source 502 may also comprise a single source and an optical grating or a single source of all light colors. Each of the sources 504 may represent a different light source and/or a different color (wavelength) of emitted light. Each of the sources 504 may be modulated, pulsed, or chopped at a slightly different frequency to cover a range of frequencies. The light beam 506 may include a plurality of separate light beams from each of the n sources 504. Alternatively, the single light beam 506 may include light emitted from each of the n sources 504. The light emitted from each of the sources 504 is scattered by the target 508 and collected and refocused by the collection optics 510 onto the detector array 512. The output from each of the n sources 504 may be detected by each of the n detectors 514, respectively. The $n^{th}$ source $504_n$ emits a light beam that is detected by the $n^{th}$ detector $514_n$. Each detector 514 in the detector array 512 may have optical coatings such that light of multiple colors may fall upon them, but each detector 514 in the detector array 512 may respond to a single color of light and reject the other colors.

In one embodiment, the array source 502 comprises a pulsed quantum cascade laser (QCL) array and the detector array 512 comprises an array of quartz crystal tuning forks (QCTF). The QCL array may include n QCLs corresponding with the n sources 504. The QCTF array may include n QCTFs corresponding with the n detectors 514. Each QCL may produce a specified optical scanning range. For each QCL in the array, there may be a corresponding QCTF. Each QCTF may be optically coated such that it will accept the range of its corresponding QCL and produce a resonant frequency different from the other QCTFs in the array. Due to the high resonant peak of the QCTFs, the QCTF array may have individual QCTFs with about a ten Hertz or more difference in resonant frequency. Each QCL may be pulsed at a frequency that approximately matches the resonant frequency of a corresponding QCTF.

The pulsed light beam 506 is scattered off the target 508 and recollected by collection optics 510, such as the parabolic mirror, or a telescope, etc. The collection optics focus the scattered light onto the detector array 512. Each detector 514 in the detector array 512 may be photoacoustically driven by the pulsed light that substantially matches its resonant frequency. The emission of beams of different optical wavelengths by each of the sources 504 from the array source 502 may occur substantially simultaneously, which may reduce the time needed to scan from one end of the spectral range to the other. Accordingly, an analysis of the target 508 over a wide spectral range may be expedited when an array of sources and array of detectors are used.

FIG. 6 illustrates a process for reverse photoacoustic standoff spectroscopy. In block 602, light is transmitted from a source to a target. The target may be a material or substance whose reflected spectrum is analyzed for providing additional information about the target. In block 604, the light source is pulsed at the detector's resonant frequency, so that the light that is transmitted from the source to the target is pulsed. When a source array is used, each of the sources may be pulsed to correspond with the resonant frequency of a corresponding detector in a detector array. The pulsed light may be transmitted with different wavelengths (colors). In block 606, the target absorbs and/or rejects light at different wavelengths. The rejected light may be scattered by the target in block 608. The scattered light may be refocused towards a detector in block 610. An optical collection device, such as a parabolic mirror or telescope, may be used to gather and refocus the scattered light. The scattered light is received at the detector in block 612.

Different types of detectors may measure or react to the scattered light. When a vibratory or oscillatory detector is used in block 614, the scattered light focused on the vibratory detector may produce an acoustic wave on the surface of the vibratory detector in block 616. The photoacoustic wave may cause the detector to vibrate in block 618. The vibration of the detector may be measured or monitored at the detector in block 620. A spectrum may be generated based on the measured photoacoustic wave for different wavelengths of emitted light as in block 620. When a photocell or photodetector is used as the detector in block 614, the scattered light is detected by the photocell in block 622. The photocell measures the intensity of the scattered light in block 624. A spectrum may be generated based on the measured light intensity for different wavelengths of emitted light as in block 626. In particular, the photocell may produce a voltage proportional to the light intensity and the spectrum may be a function of the photocell voltage versus the optical wavelength of the light.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description. While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A standoff spectroscopy system comprising:
   a light source that emits pulsed light;
   a target that is illuminated by the light source, wherein at least some of the pulsed light at the target is scattered, reflected, or refracted;
   a vibratory detector that measures the scattered pulsed light from the target, wherein a photoacoustic wave is produced on a surface of the detector creating a mechanical vibration of the detector that is used to measure the intensity of the scattered pulsed light as the optical frequency of the light is varied; and
   a collection optic that focuses the scattered, reflected, or refracted light onto the vibratory detector;
   wherein the target is located away from the light source and the detector in the standoff spectroscopy system.

2. The system of claim 1 wherein an amplitude of the vibration of the detector is used to measure the intensity of the scattered pulsed light as the optical frequency of the light is varied.

3. The system of claim 1 wherein a frequency of the pulsed light corresponds with a resonant frequency of the vibratory detector.

4. The system of claim 1 wherein the pulsed or chopped light creates an acoustic wave on the surface of the vibratory detector.

5. The system of claim 4 wherein the detector comprises of any mechanical resonator and the pulse or chop frequency of the light corresponds with the resonant frequency of the mechanical resonator.

6. The system of claim 5 wherein the light source comprises of any light source.

7. The system of claim 1 wherein an analysis of the reversed photoacoustic spectrum identifies the target.

8. A standoff spectroscopy system comprising:
   a quantum cascade laser light source that emits pulsed light;
   a target that is illuminated by the light source; wherein at least some of the pulsed light at the target is scattered; and
   a quartz crystal tuning fork distanced from the target, the quartz crystal tuning fork being used as a detector that measures the scattered pulsed light from the target, wherein the scattered pulsed light from the target produces a photoacoustic wave on the surface of the detector creating a mechanical vibration of the detector.

9. The system of claim 8 wherein the scattered pulsed light is reflected or refracted from the target.

10. The system of claim 8 wherein the quartz crystal tuning fork is optically coated for increased absorbance by the pulsed light beam and/or placed in an environment which enhances effects of the tuning fork.

11. The system of claim 8 further comprising a collection optic that focuses the scattered pulsed light onto at least one tine of the quartz crystal tuning fork.

12. The system of claim 8 wherein an amplitude of the vibration of the detector is used to measure an intensity of the scattered pulsed light as the optical frequency of the light is varied.

13. The system of claim 8 wherein a frequency of the pulsed light corresponds with a resonant frequency of the quartz crystal tuning fork.

14. The system of claim 8 wherein the light beam is pulsed at varying frequencies and an intensity of the photoacoustic wave is used to create a spectrum at the varying frequencies.

15. The system of claim 14 wherein an analysis of the reversed photoacoustic spectrum identifies the target.

16. A system for standoff spectroscopy comprising:
   a target;
   a source array comprising a plurality of sources that each emit a pulsed light beam with different pulse frequencies onto the target at a predetermined frequency; and
   a detector array located a distance from the target, the detector array comprising a plurality of detectors that each have a predetermined resonant frequency, wherein the resonant frequency for each of the detectors corresponds with the predetermined frequency from one of the sources, further wherein each of the detectors measures, on a surface of that detector, an optical scattering, reflection, or refraction by the target of the pulsed light beam from the corresponding one of the sources.

17. The system of claim 16 further comprising a collection optic that focuses the reflected light from the target to the detector array.

18. The system of claim 16 wherein the measurement at each of the detectors comprises an acoustic or vibrational measurement generated on the surface of the detector.

19. The system of claim 18 wherein a spectrum of the measurement is generated based on the measured vibrational intensity at the predetermined frequencies of each of the sources.

20. A system for standoff spectroscopy of a target comprising:
   a quantum cascade laser array that emits pulsed light beams onto the target;
   a collection optic that receives scattered, reflected, and/or refracted light from the pulsed light beams being rejected by the target; and
   a quartz crystal tuning fork array that receives the scattered, reflected, and/or refracted light from the collection optic and generates a vibration on each of the quartz crystal tuning forks in the array.

21. The system of claim 20 wherein the quartz crystal tuning fork array is optically coated for increased absorbance by the pulsed light beams and/or placed in an environment which enhances effects of each tuning fork in the array.

22. The system of claim 20 wherein the collection optic focuses the scattered, reflected, or refracted light onto the quartz crystal tuning fork array.

23. The system of claim 19 wherein an acoustic wave is generated on the surface from the scattered or reflected pulsed light of the quartz crystal tuning fork driving the quartz crystal tuning fork into a mechanical vibration that is measured.

24. The system of claim 20 wherein the light beam is tuned to different optical frequencies and the intensity of the acoustic wave on the surface of the quartz crystal tuning fork is used to create a spectrum at the different optical frequencies.

* * * * *